(12) United States Patent
Turner et al.

(10) Patent No.: US 8,480,168 B2
(45) Date of Patent: *Jul. 9, 2013

(54) OPERATING SUPPORT FOR SURGEONS

(75) Inventors: Craig Turner, Portland, OR (US); John Economaki, Lake Oswego, OR (US)

(73) Assignee: Ethos Surgical, LLC, Vancouver, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/287,625

(22) Filed: Nov. 2, 2011

(65) Prior Publication Data
US 2012/0043790 A1 Feb. 23, 2012

Related U.S. Application Data

(63) Continuation of application No. 12/194,388, filed on Aug. 19, 2008, now Pat. No. 8,070,221.

(60) Provisional application No. 60/965,791, filed on Aug. 21, 2007.

(51) Int. Cl.
*B60N 2/38* (2006.01)

(52) U.S. Cl.
USPC ............... 297/195.11; 297/423.12; 297/411.1

(58) Field of Classification Search
USPC ............... 297/423.1, 423.12, 411.36, 411.33, 297/411.38, 195.11
See application file for complete search history.

(56) References Cited

U.S. PATENT DOCUMENTS

| | | | |
|---|---|---|---|
| 3,029,106 A | 4/1962 | McGuire | |
| 3,337,261 A | 8/1967 | Nihlean et al. | |
| 3,754,787 A | 8/1973 | Garber | |
| 4,699,423 A * | 10/1987 | Fitzig et al. | 297/245 |
| 5,029,941 A | 7/1991 | Twisselmann | |
| 5,490,716 A * | 2/1996 | Naughton | 297/423.12 |
| 5,542,746 A * | 8/1996 | Bujaryn | 297/423.12 |
| 5,725,280 A | 3/1998 | Kushnir | |
| 6,203,109 B1 * | 3/2001 | Bergsten et al. | 297/411.35 |

(Continued)

FOREIGN PATENT DOCUMENTS
DE 19504838 A1 7/1995

OTHER PUBLICATIONS

Schurr et al., "Ergonomic Surgeon's Chair for Use During Minimally Invasive Surgery," *Surg Laparosc Endosc Percutan Tech.*, 9(4): 244-247, 1999.

(Continued)

*Primary Examiner* — David Dunn
*Assistant Examiner* — Erika Garrett
(74) *Attorney, Agent, or Firm* — Klarquist Sparkman, LLP

(57) ABSTRACT

The present disclosure concerns embodiments of an operating support that supports a surgeon in a sitting position straddling a patient. By straddling the patient, the surgeon is ideally positioned to perform certain types of laparoscopic surgery, such as pelvic surgery, which requires the use of relatively long surgical instruments. The operating support supports the surgeon in a more ergonomically correct position that reduces the stress and strain on the surgeon's body as compared to the conventional technique of performing laparoscopic surgery in a standing position at one side of the operating table.

25 Claims, 11 Drawing Sheets

U.S. PATENT DOCUMENTS

| | | | |
|---|---|---|---|
| 6,224,154 B1* | 5/2001 | Stoki | 297/339 |
| 6,532,595 B1* | 3/2003 | Holmes | 2/48 |
| 6,565,154 B2 | 5/2003 | Davis | |
| 6,595,590 B2 | 7/2003 | Bottoms | |
| 6,619,747 B2* | 9/2003 | Ko et al. | 297/423.12 |
| 6,773,071 B1* | 8/2004 | Stasney et al. | 297/411.27 |
| 6,902,178 B2 | 6/2005 | Wing | |
| 6,957,718 B1 | 10/2005 | Whiteside et al. | |
| 7,195,583 B2 | 3/2007 | Leib | |
| 7,240,964 B2* | 7/2007 | Riley | 297/229 |
| 8,070,221 B2* | 12/2011 | Turner et al. | 297/195.11 |
| 2004/0189071 A1 | 9/2004 | Komura et al. | |

OTHER PUBLICATIONS

International Search Report and Written Opinion of the International Searching Authority, mailed Jul. 6, 2009, for corresponding International Application No. PCT/US2008/074669.

Office Action from the United States Patent & Trademark Office in co-pending U.S. Appl. No. 12/194,388, dated May 19, 2011.

Notice of Allowance from the United States Patent & Trademark Office in co-pending U.S. Appl. No. 12/194,388, dated Sep. 2, 2011.

European Patent Office, "Communication—European Examination Report" for European Application No. EP08 798 893.7-1269, Dec. 12, 2011, 5 pages.

* cited by examiner

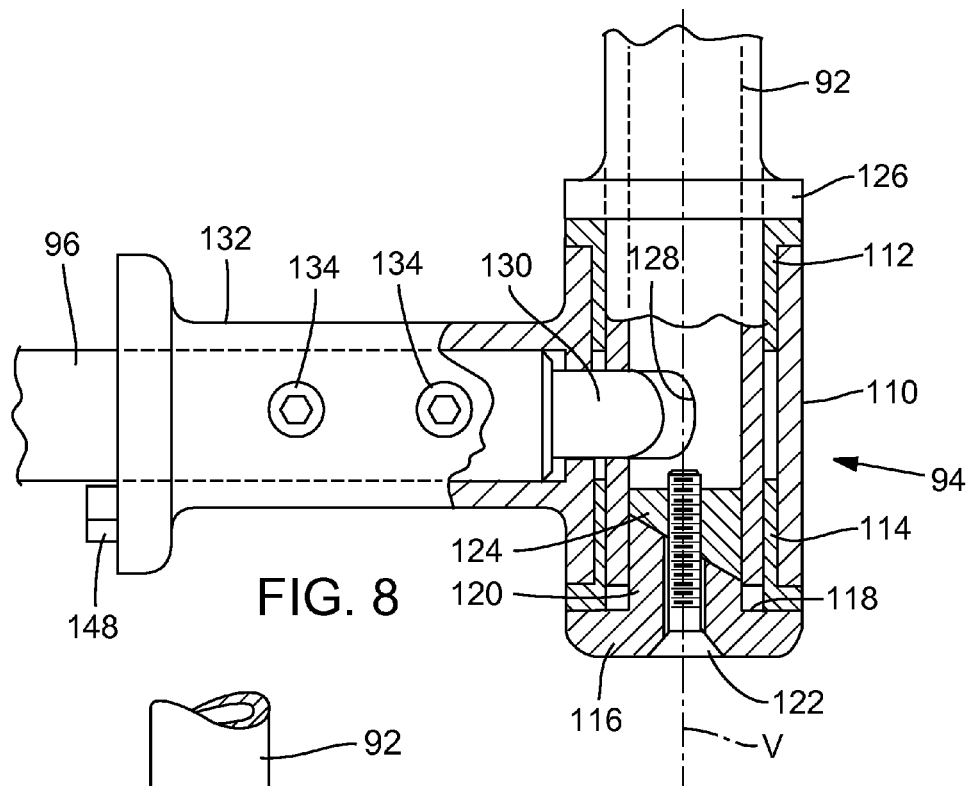
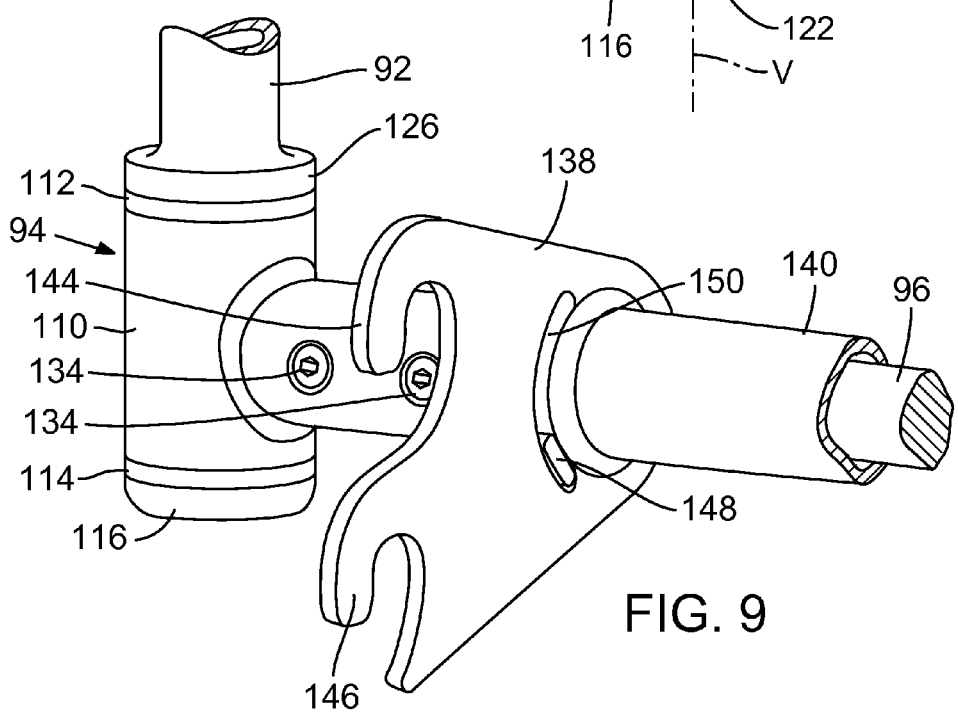

OPERATING SUPPORT FOR SURGEONS

CROSS REFERENCE TO RELATED APPLICATION

The present application is a continuation of U.S. patent application Ser. No. 12/194,388, filed Aug. 19, 2008, now U.S. Pat. No. 8,070,221, which claims the benefit of U.S. Provisional Application No. 60/965,791, filed Aug. 21, 2007, both of which are incorporated herein by reference.

FIELD

The present disclosure concerns embodiments of an operating support for a surgeon performing a medical procedure (e.g., surgery) on a patient.

BACKGROUND

During laparoscopic surgery, the surgeon typically stands to one side of the operating table while manipulating relatively long instruments and while viewing the procedure on a video monitor. Unfortunately, the surgeon has little opportunity to move the body and change posture, which often leads to fatigue and pain. Thus, there is a strong need for an apparatus to support the surgeon during such procedures in a manner that reduces the stress and strain on the surgeon's body.

SUMMARY

The present disclosure concerns embodiments of an operating support that supports a surgeon in a sitting position straddling a patient. By straddling the patient, the surgeon is ideally positioned to perform certain types of laparoscopic surgery, such as pelvic surgery, which requires the use of relatively long surgical instruments. The operating support places the surgeon in a more ergonomically correct position that reduces the stress and strain on the surgeon's body as compared to the conventional technique of performing laparoscopic surgery in a standing position at one side of the operating table. The position of the surgeon relative to the patient also provides other doctors or nurses access to the patient during the procedure, for example if the anesthesiologist must attend to the patient.

The operating support in disclosed embodiments includes a frame structure that supports a seat such that an end portion of an operating table can be positioned directly underneath the seat to allow the surgeon to straddle a patient positioned on (e.g., lying down) the operating table. The seat can be vertically adjustable relative to the frame structure to allow the seat to be positioned at a desired height relative to the patient. The operating support also can include foot supports for supporting the surgeon's feet, a chest support for supporting the surgeon's chest, and arm supports for supporting the surgeon's arms. The foot supports, the chest support, and the arm supports also can be vertically adjustable to suit the individual needs of the surgeon.

The frame structure desirably has light-weight construction so that the operating support can be easily positioned for use and transported between operating theaters. In certain embodiments, the frame structure can be constructed from tubular frame members and desirably is made from a light-weight material such as steel, aluminum or any of various other suitable metals, alloys, polymers, or composite materials. This provides a light-weight construction allowing for easy positioning and transporting of the operating support. If it becomes necessary during surgery to provide additional access to the patient, for example if the anesthesiologist requires additional access to the patient, the surgeon can quickly dismount the operating support. The operating support then can be easily moved away from the patient to provide other doctors or nurses additional access the patient.

In one representative embodiment, an operating support for a surgeon performing a medical procedure on a patient positioned on an operating table comprises a seat adapted to support the buttocks of the surgeon and a frame structure supporting the seat. The frame structure is configured to be positioned relative to the operating table such that the seat is positioned over the operating table and the surgeon, while sitting in the seat, can straddle the patient.

In another representative embodiment, an operating support for a surgeon performing a medical procedure on a patient positioned on an operating table comprises a frame structure comprising first and second laterally spaced, vertically extending support members, and a seat supported between the first and second support members. The support members are spaced from each other such that an end portion of the operating table can be positioned between the support members and beneath the seat to allow the surgeon to straddle the patient at a position above and over the patient.

In another representative embodiment, a surgical system comprises an operating table for supporting a patient, and a support apparatus for a surgeon performing a medical procedure on the patient. The support apparatus comprises a seat adapted to support the buttocks of the surgeon, and means for supporting the seat at a position over and above an end portion of the operating table such that the surgeon, while sitting in the seat, can straddle the patient.

In another representative embodiment, a method of performing a medical procedure on a patient positioned on an operating table is provided. The method comprises sitting on an operating support at a position above and over the patient while straddling the patient, and performing a surgical procedure on the patient.

The foregoing and other features and advantages of the invention will become more apparent from the following detailed description, which proceeds with reference to the accompanying figures.

BRIEF DESCRIPTION OF THE DRAWINGS

FIG. 8 is an elevation view of the lower end portion of one of the arm supports and one end portion of the shaft of the arm support assembly.

FIG. 9 is a perspective view of the lower end portion of one of the arm supports and one end of the bracket assembly that supports the arm support assembly on the operating support.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but may optionally contain C or other components other than A and B. A device that includes or comprises A or B may contain A or B or A and B, and optionally one or more other components such as C.

Referring first to FIGS. 1-4, there is shown one embodiment of an operating support, or saddle, indicated generally at 10, that supports a surgeon in an ergonomically correct position for performing certain types of medical procedures, and in particular surgical procedures. The operating support 10 can be used while performing surgery on a patient positioned on (e.g., lying down) an operating table (e.g., the operating table 12 shown in FIGS. 13 and 14) or on a patient chair that can recline (e.g., a dentist chair) to position the patient in a lying-down or near lying-down position. The operating support 10 can be used to support the surgeon in a seated position straddling the patient to reduce stress and strain on the surgeon's body while performing certain types of surgery, especially laparoscopic surgery (e.g., pelvic surgery). The support can used for performing various other types of procedures, including, without limitation, interventional radiology procedures, maxillo-facial surgery, abdominal surgery, cardiac surgery, thoracic surgery, dental procedures, neurosurgical procedures, and orthopedics, to name a few.

Figure 13:
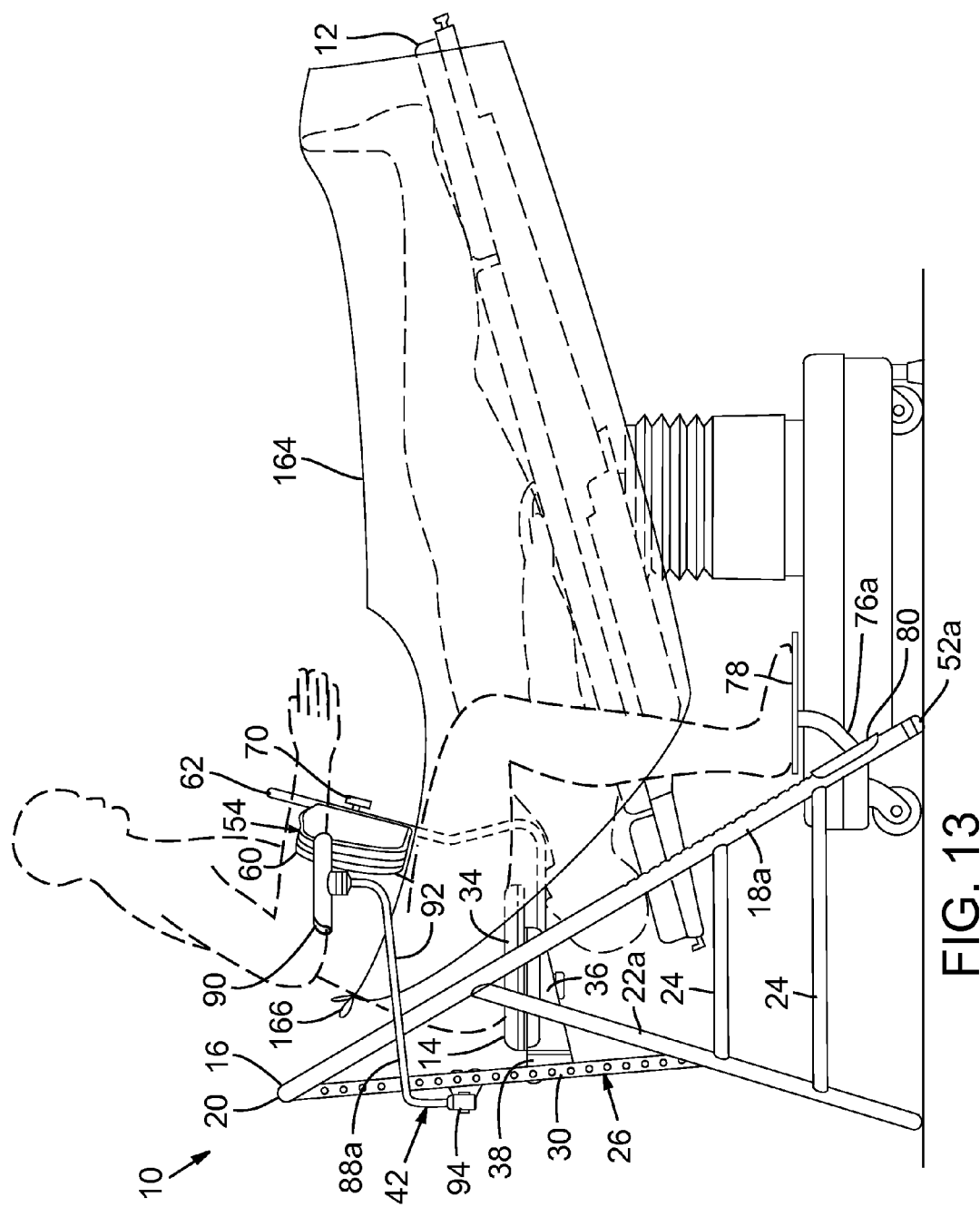
FIG. 13 is a side view of the operating support of FIG. 1 being used to support a surgeon in a position straddling a patient lying on an operating table.
Figure 14:
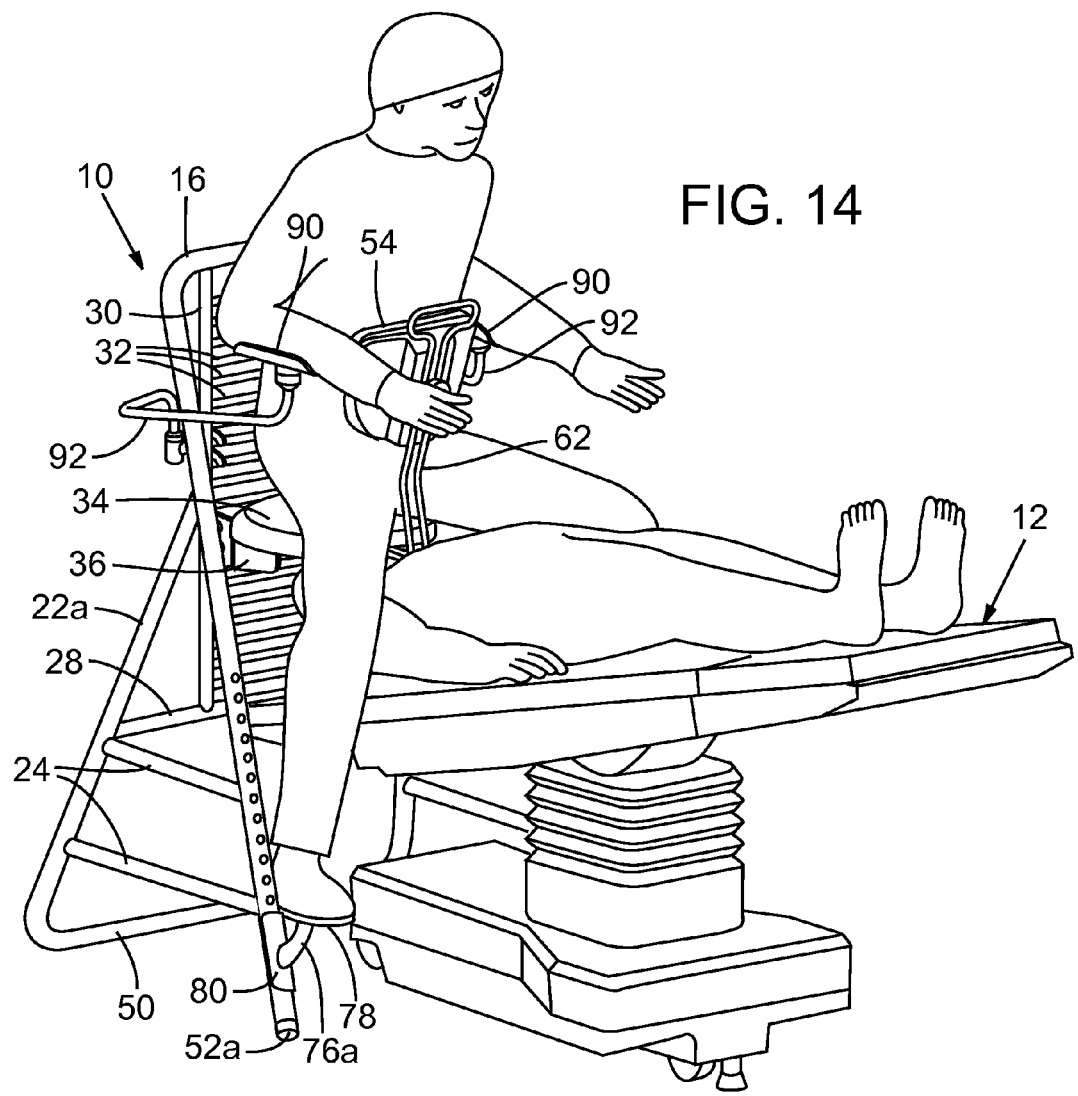
FIG. 14 is a perspective view of the operating support and operating table shown in FIG. 13.

The operating support 10 in the illustrated embodiment includes a seat 14 adapted to support the buttocks of the surgeon and a frame structure 16 that supports the seat 14. The frame structure 16 is configured to be positioned relative to the operating table 12 such that the seat 14 can be positioned above and over an end portion of the table 12 as illustrated in FIGS. 13 and 14.

Figure 2:
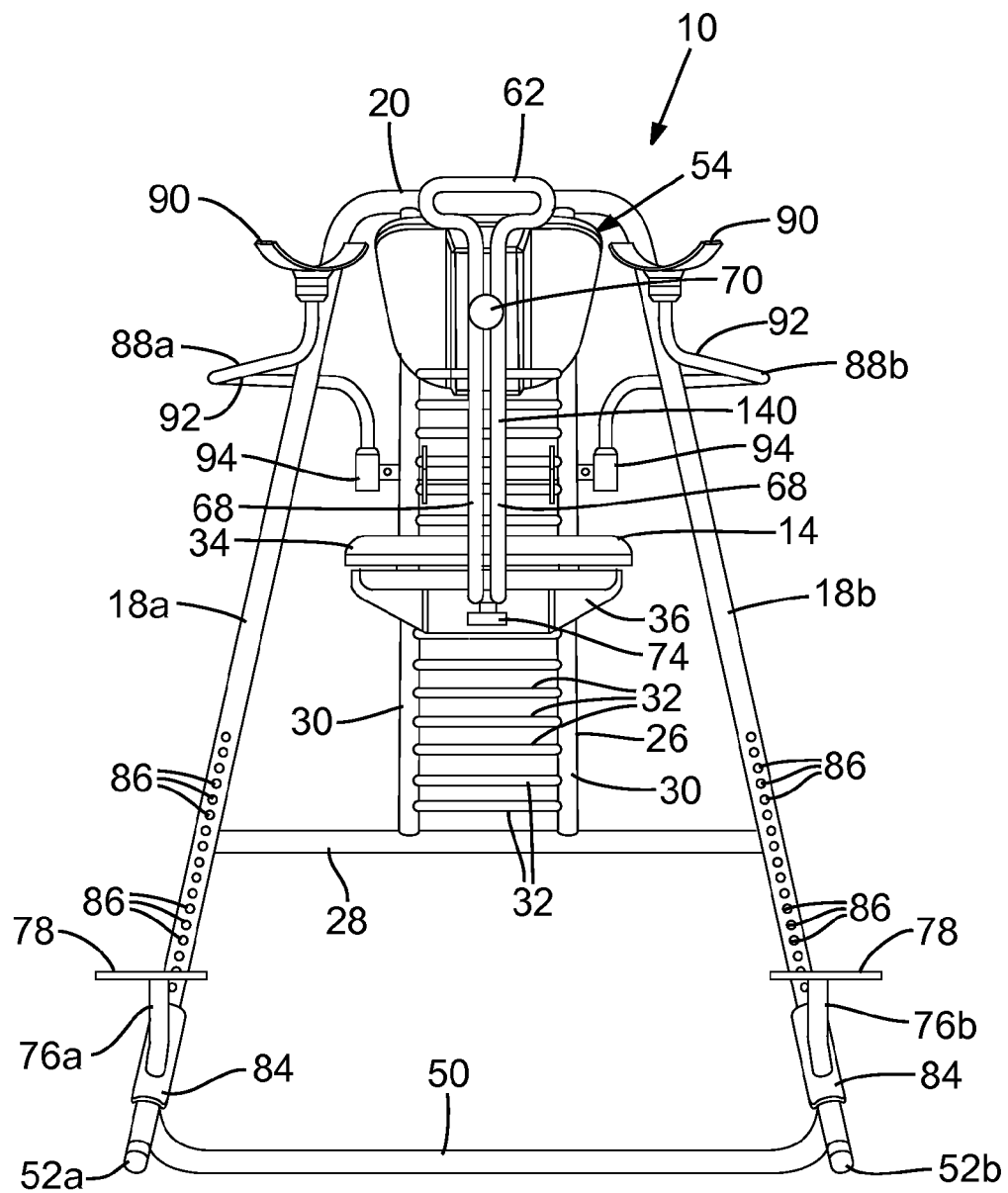
FIG. 2 is a front view of the operating support shown in FIG. 1.
Figure 3:
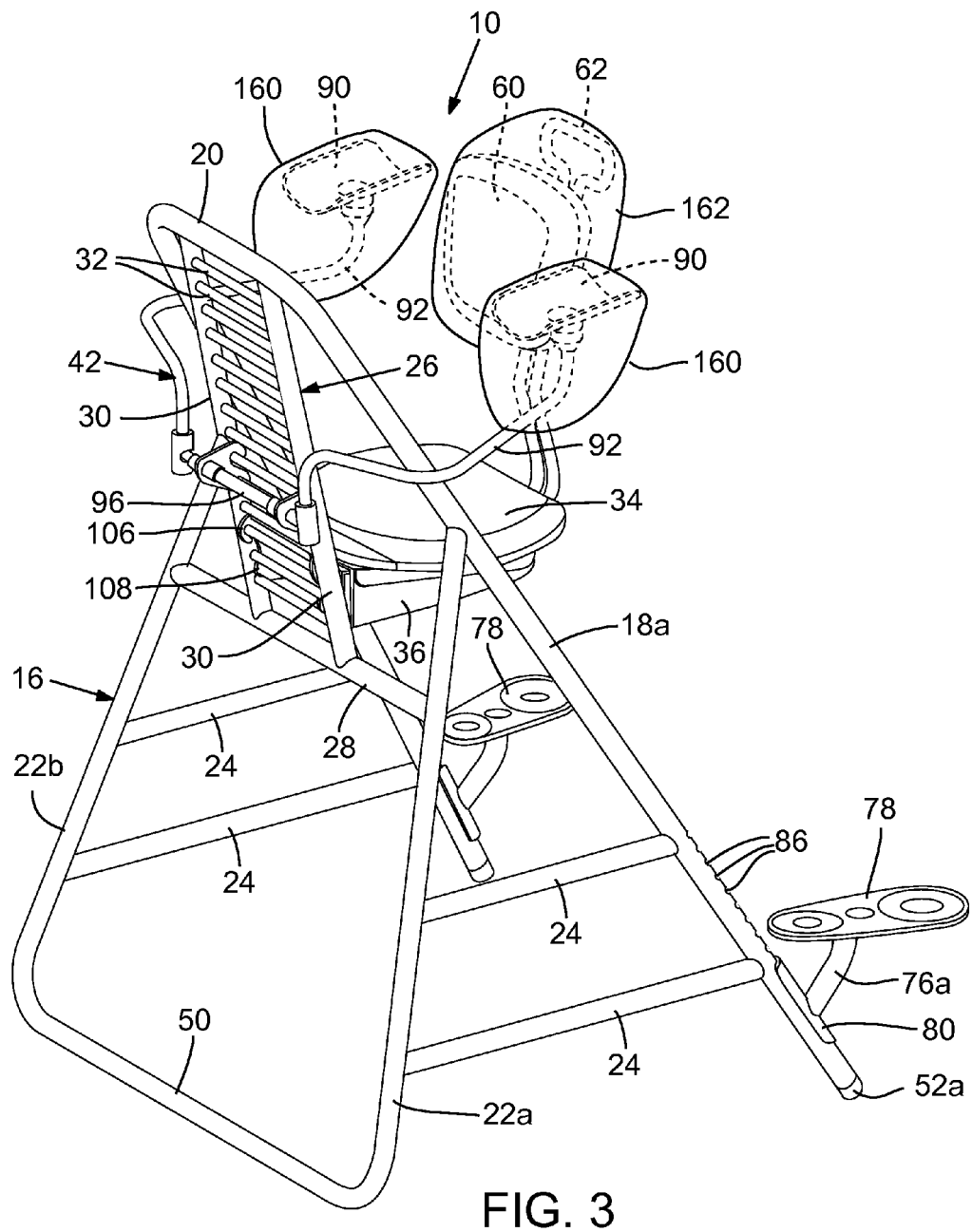
FIG. 3 is a perspective view of the operating support shown in FIG. 1.
Figure 4:
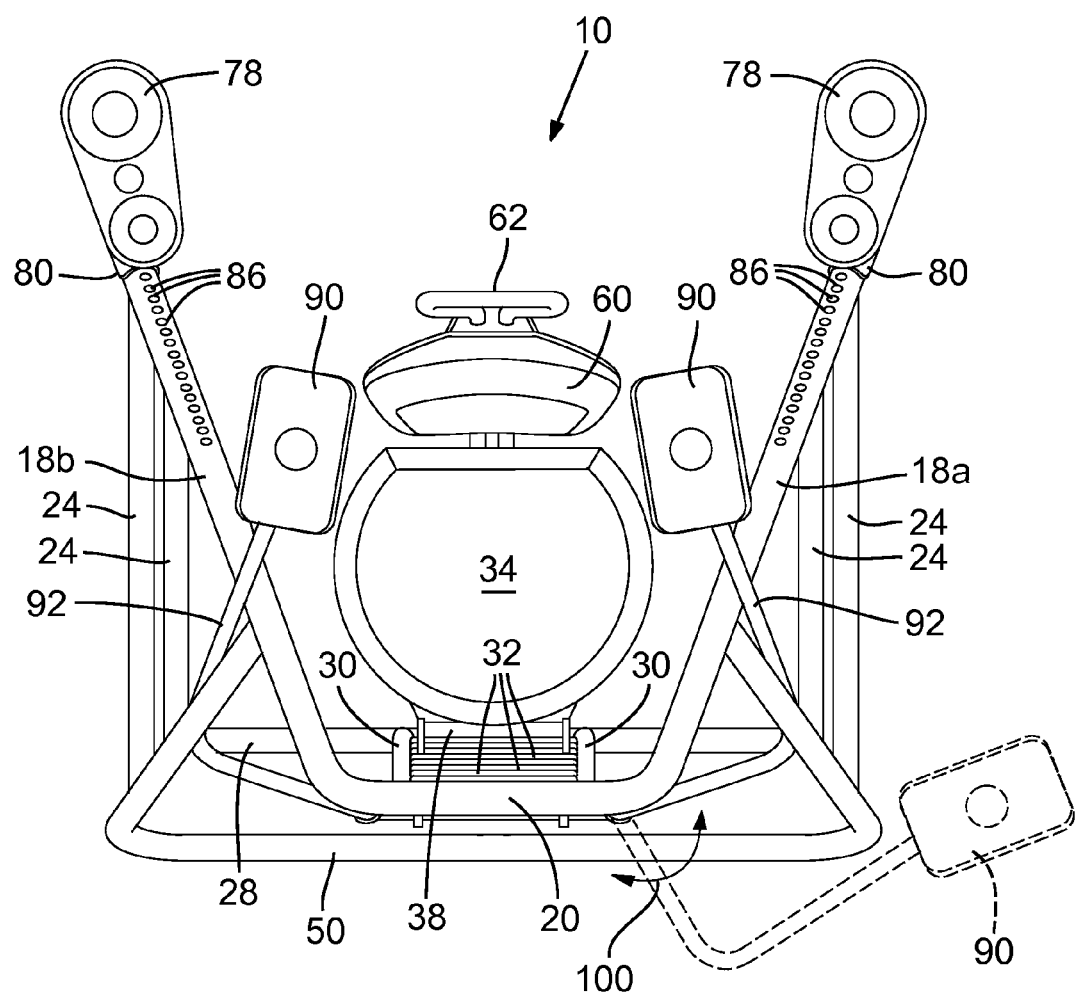
FIG. 4 is a top plan view of the operating support shown in FIG. 1.

As best shown in FIGS. 1-4, the frame structure 16 in particular embodiments includes first and second main support members 18a, 18b, respectively, positioned on opposite sides of the seat 14. The support members 18a, 18b can be connected to each other by a cross member 20 at the top of the frame structure and can extend downwardly and forwardly from the cross member 20. As best shown in FIG. 4, the support members 18a, 18b also can extend laterally outwardly away from the seat moving in a direction toward the floor to provide a larger footprint at the base of the frame structure for better stability. The support members 18a, 18b are laterally spaced from each other on opposite sides of the seat a distance sufficient to allow an end portion of the operating table 12 to be positioned between the support members and underneath the seat 14. This allows the surgeon to be supported in a seated position straddling the patient, as depicted in FIGS. 13 and 14.

As shown in FIG. 3, the frame structure 16 additionally can include rear support members 22a, 22b having upper ends connected to the support members 18a, 18b and lower ends supported on the floor. The lower ends of the rear support members 22a, 22b can be connected to each other by a lower cross member 50. One or more cross members 24 can extend between the main support member 18a and the rear support member 22a and between the main support member 18b and the rear support member 22b.

The lower ends of the support members 18a, 18b can have support pads 52a, 52b, respectively, contacting the floor (FIG. 2). The support pads 52a, 52b can be made of a low-friction material, for example a low-friction polymer such as high density polyethylene or Delron®, so that the support 10 can be easily moved in the operating theater. In alternative embodiments, the lower ends of the support members 18a, 18b and/or the lower ends of the rear support members 22a, 22b can include wheels to facilitate positioning and transporting the support 10. Such wheels can be provided with locks to prevent the wheels from the moving during surgery.

As best shown in FIGS. 2 and 3, the frame structure 16 in particular embodiments can also include a support frame assembly 26 (also referred to herein as a seat support member), which can have an upper end connected to the cross member 20 and a lower end connected to a cross member 28 extending between and connected to the rear support members 22a, 22b. The support frame assembly 26 in the illustrated embodiment includes elongated vertical posts 30 extending vertically between cross members 20 and 28 and a plurality of vertically spaced, horizontally disposed rungs, or bars, 32 extending between and connected to the vertical posts 30.

The seat 14 can include a seat cushion 34 and a seat frame 36 supporting the seat cushion. The seat frame 36 desirably is vertically adjustable to adjust the height of the seat along the support frame assembly 26. For example, the seat frame 36 can include a rear portion 38 (FIG. 1) that is configured to be removably mounted to the rungs 32. The seat can be easily adjusted to a desired height by removing the seat frame 36 from support frame assembly 26 and placing the seat frame 36 on rungs 32 at a desired height.

Figure 5:
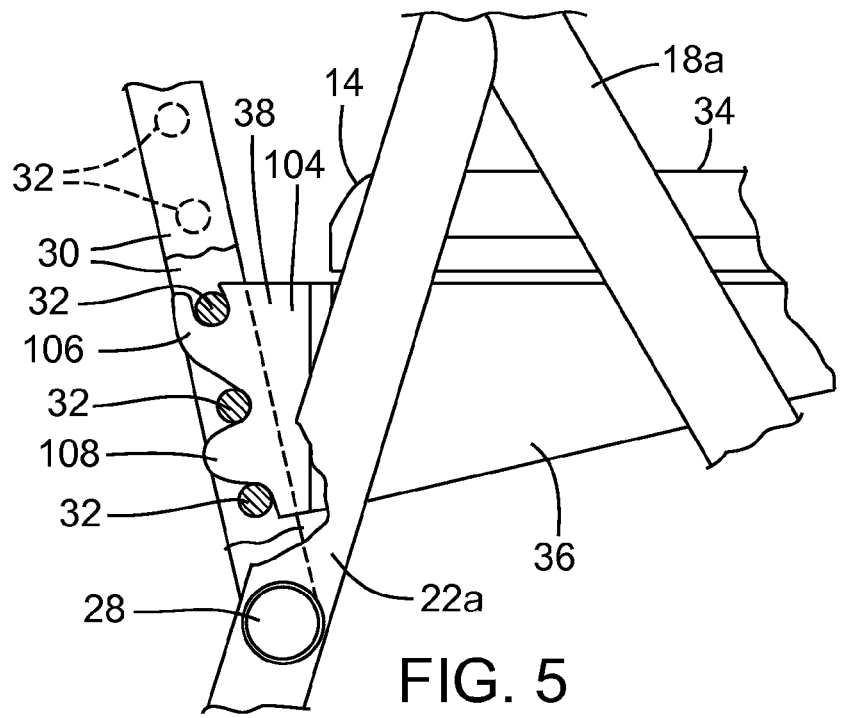
FIGS. 5 and 6 are side views showing how the seat can be removed from the operating support.

FIG. 5 is an enlarged view of the rear end portion 38 of the seat frame 36, according to one embodiment. The rear end portion 38 can be formed from two laterally spaced side plates 104, each of which is positioned adjacent a respective post 30 of the support frame assembly 26. As shown, each side plate 104 can be formed with an upwardly curved protrusion, or hook portion, 106 that extends between two adjacent rungs 32. Each side plate 104 can also be formed with another protrusion 108 that extends between two adjacent rungs 32 below protrusion 106. By virtue of the engagement of the protrusions 106, 108 with the rungs 32, the seat 14 is retained in a horizontal position against the weight of the user.

Figure 6:
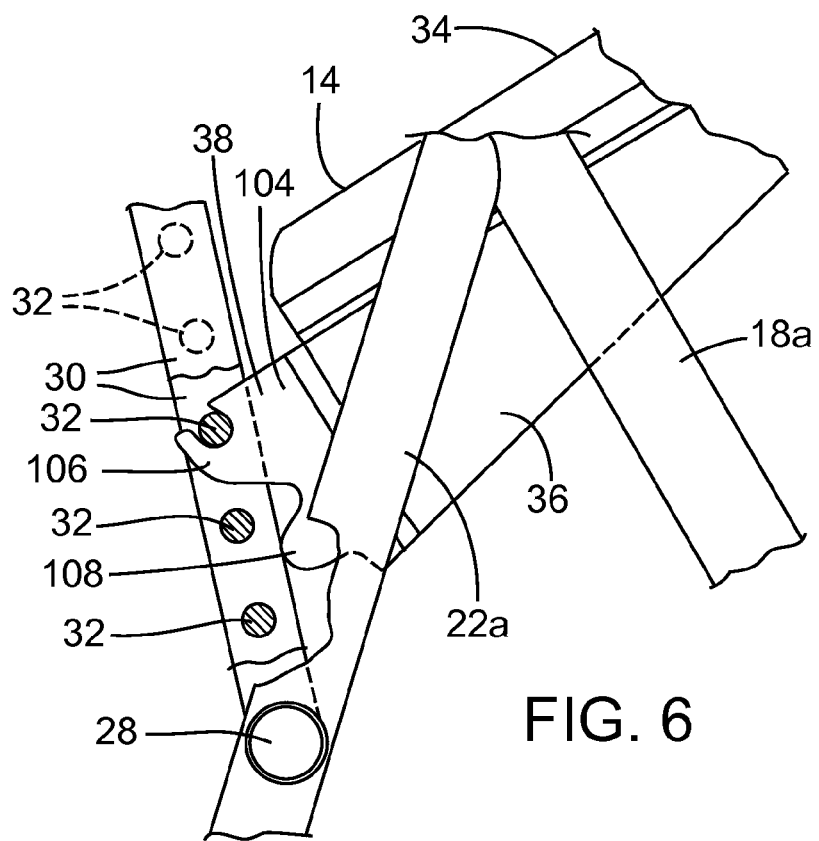

As shown in FIG. 6, the seat 14 can be removed from the support frame assembly 26 by lifting the front end of the seat upwardly until the lower protrusion 108 clears the corresponding rungs 32, and then sliding the seat downwardly to remove the upper protrusion 106 from the corresponding rungs 32. Other techniques or mechanisms can be used to permit the seat 14 to be vertically adjustable. For example, the seat can be mounted on a vertical screw mechanism that is operable to adjust the height of the seat.

Referring again to FIG. 1, the operating support 10 can include a chest support 54 adapted to support the chest of the surgeon during use. The chest support desirably is adjustable in the forward and rearward directions (as indicated by double-headed arrow 56 in FIG. 1) as well as upwardly and downwardly (as indicated by double-headed arrow 58 in FIG. 1) to satisfy the individual needs and preferences of the surgeon. In the illustrated embodiment, for example, the chest support 54 includes a chest support pad 60 that is supported on and adjustable relative to a chest-support frame 62. The frame 62 in the illustrated form includes a horizontal lower portion 64 extending from and connected to the seat frame 36 and a vertical upper portion 66 extending upwardly from the forward end of the lower portion 64. The lower portion 64 and the upper portion 66 can be formed from two parallel, elongate frame members 68, as best shown in FIG. 2. The chest pad 60 can be adjustably mounted to the frame 62 by an adjustment knob 70 that has a threaded shaft that extends through the frame members 68 and into a threaded opening in the chest pad. The chest pad 60 can be adjusted to a desired height along the frame members 68 by loosening the knob 70, sliding the chest pad 60 to the desired height, and then tightening the knob 70 to secure the chest pad in place against the frame members 68.

The chest support 54 can be similarly adjusted in the fore-aft direction (toward and away from the front of the seat). For example, as shown in FIG. 2, the chest-support frame 62 can be secured to the lower surface of the seat frame 36 by an adjustment knob 74 having a threaded shaft 76 that extends through frame members 68 and into a threaded opening in the lower surface of the seat frame 36. The knob 74 can be loosened to permit fore-aft adjustment of the chest-support frame 62 relative to the seat frame. Tightening the knob 74 secures the chest-support frame 62 to the seat frame at the desired fore-aft position.

Furthermore, in certain embodiments, the angle of the chest support 54 relative to a vertical plane can be adjusted to allow the user to lean closer to or farther away from the patient. For example, the upwardly extending frame portion that supports the chest support (e.g., upper portion 66) can be pivotably mounted at its lower end portion to permit pivoting of the frame portion and the chest support 54 relative to a vertical plane. Any suitable techniques or mechanisms can be used to permit pivoting of the frame portion to a desired angle relative to the vertical plane and to lock the frame portion at the desired position. In one implementation, a push button, lever, or similar control mechanism can be used such that activation of the control mechanism is effective to allow pivoting of the chest support to a desired position and release of the control mechanism retains the chest support at the desired position, similar to the controls used to adjust the position of a seat in an automobile.

Figure 1:
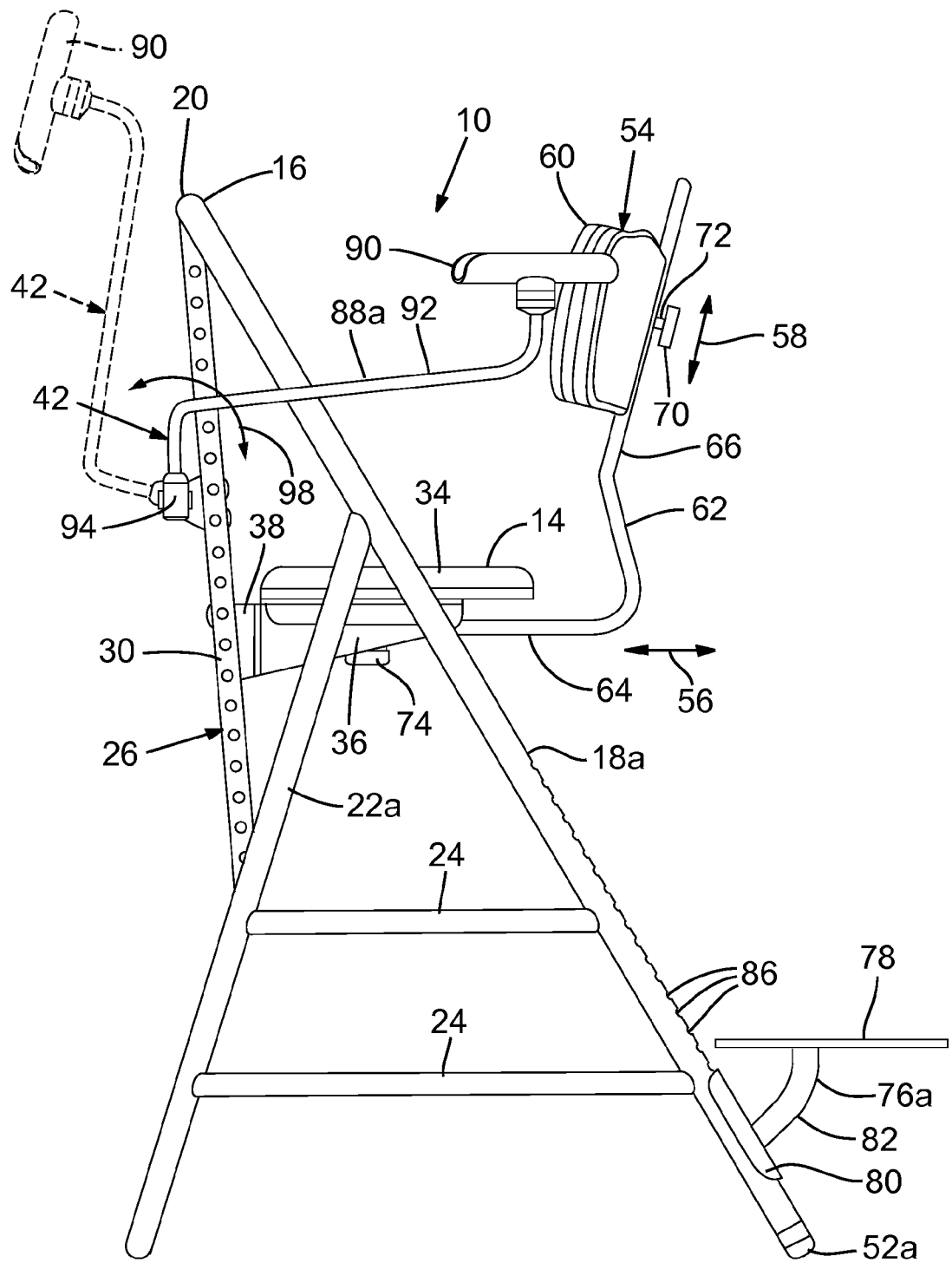
FIG. 1 is a side view of an operating support for a surgeon, according to one embodiment.

The operating support 10 can include first and second foot supports 76a, 76b adapted to the support the right and left feet, respectively, of the surgeon. The foot supports 76a, 76b desirably are vertically adjustable to satisfy the particular needs of the user. For example, in the illustrated embodiment, the foot supports 76a, 76b are mountable to and adjustable along the length of the support members 18a, 18b. As best shown in FIG. 1, each foot support 76a, 76b can include a horizontally disposed foot pad 78, a bracket 80 and an extension arm 82 extending between and connecting the foot pad to the bracket. To permit vertical adjustment of the foot supports, each bracket 80 can be formed with a plurality of pins or prongs (not shown) that can be inserted into apertures 86 formed along the length of the respective support member 18a, 18b. Other techniques or mechanisms also can be used to mount foot supports 76a, 76b to the support members 18a, 18b. For example, the brackets 80 can be secured to support members 18a, 18b with bolts, screws, or other types of fasteners.

The operating support can further include an arm support assembly 42 coupled to and supported by the frame structure 16. The arm support assembly 42 can include first and second arm supports 88a, 88b for supporting the arms of the surgeon. Each arm support 88a, 88b can include an arm rest 90 mounted on the forward end of a support arm 92. As best shown in FIG. 2, the support arm 92 of each support 88a, 88b extends downwardly from the respective arm rest 90 and rearwardly toward the seat support member 26. The lower end portion of each support arm 92 can be connected to a respective pivot mechanism 94. The pivot mechanisms 94 are connected to opposite ends of a shaft 96 (FIG. 7), which in turn can be removably mounted to the support frame assembly 26.

Each pivot mechanism 94 can be configured to permit pivoting movement of the respective arm support 88a, 88b about two separate pivot axes. For example, in the illustrated embodiment, each pivot mechanism 94 allows for pivoting movement of the respective arm support about a vertical pivot axis and a horizontal pivot axis. This allows each arm support to be pivoted upwardly and downwardly about a horizontal pivot axis between a lowered position (shown in solid lines in FIG. 1) adjacent the surgeon and a raised position away from surgeon (shown in dashed lines in FIG. 1), in the directions indicated by double-headed arrow 98 in FIG. 1. Each arm support also can be pivoted about a respective vertical axis between a forward position (shown in solid lines in FIG. 4) adjacent the surgeon and a rearward position (shown in dashed lines in FIG. 4) away from surgeon, independent of pivoting movement about its horizontal axis, as indicated by double-headed arrow 100.

Figure 7:
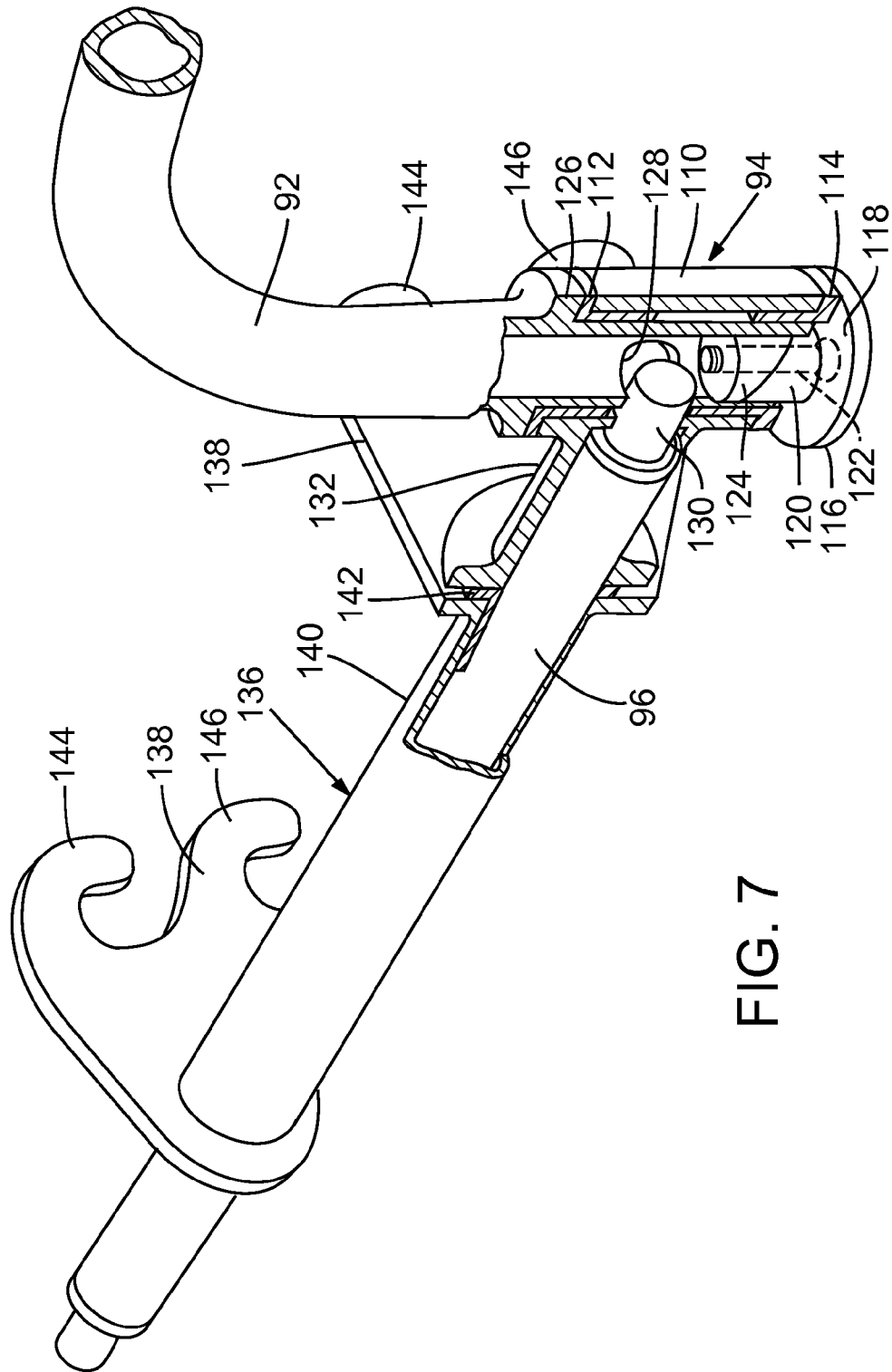
FIG. 7 is a perspective view of the arm support assembly of the operating support shown partially in section.

As best shown in FIG. 7, each pivot mechanism 94 in the illustrated embodiment comprises a bearing housing 110 that receives the lower end portion of a respective support arm 92. The pivot mechanism 94 can include an upper bearing 112 and a lower bearing 114 retained between the housing 110 and the lower portion of the support arm 92. The housing 110 and the bearings 112, 114 can be retained on the lower end portion of the support arm 92 by a tapered lock nut assembly.

The lock nut assembly in the illustrated embodiment comprises a cap portion 116 having an enlarged head portion 118 and an extension portion 120 that extends into the lower portion of the support arm 92. A screw 122 extends through a threaded opening in the cap portion 116 and a corresponding threaded opening in a tapered nut 124. The nut 124 has an angled lower surface that bears against an angled upper surface of the extension portion 120. When the screw 122 is tightened, the nut 124 rotates relative to the cap portion 116. By virtue of the angled surfaces of the nut 124 and the extension portion 120, the nut 124 is urged against the inner surface of the support arm 92, securing the lock nut assembly at the lower end of the support arm 92. The lock nut assembly retains the bearings and the bearing housing in place between the head portion 118 and a flange member 126 of the support arm 92 while allowing pivoting movement of the support arm 92 relative to the bearing housing about a vertical pivot axis V (FIG. 8).

Figure 11:
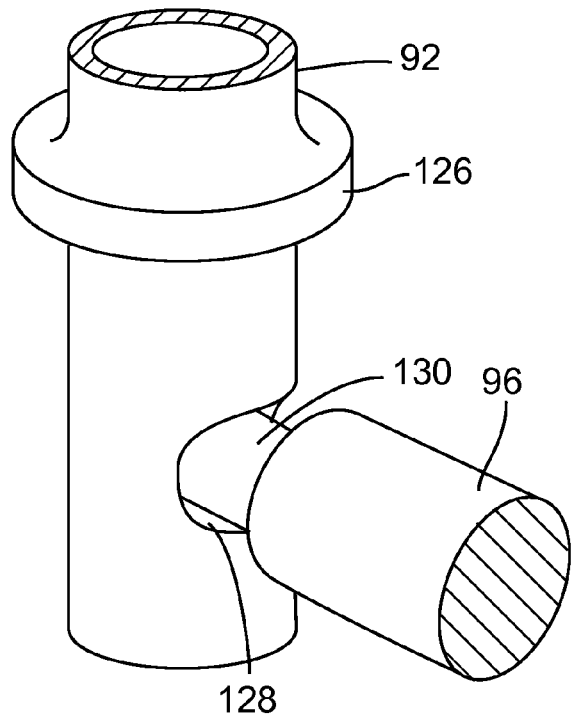
FIG. 11 is a perspective view of the lower end portion of one of the arm supports and one end portion of the shaft of the arm support assembly shown with the bearing housing removed for purposes of illustration.

As best shown in FIG. 11, the lower end portion of the support arm 92 can be formed with an elongated opening 128 that receives the adjacent end portion 130 of the shaft 96. The arc length of the opening 130 defines the angle through which the support arm 92 can pivot about its vertical axis V. The shaft end portion 130 serves as a stop that limits pivoting movement of the support arm 92 about its vertical pivot axis. Thus, as the support arm is pivoted about its vertical axis, the shaft end portion 130 can contact the opposing sides of the opening 130 to limit pivoting of the support arm 92 between the forward and rear positions shown in FIG. 1.

Referring again to FIG. 7, the bearing housing 110 in the illustrated configuration can include a horizontally extending, shaft-receiving portion 132 that houses an adjacent portion of the shaft 96. As best shown in FIG. 9, the shaft 96 can be fixedly secured to the bearing housing 110 by a screw 134 that extends through the shaft-receiving portion 132 and is tightened into a threaded opening in the shaft 96. In this manner, both support arms 92 pivot together about the horizontal axis defined by the shaft 96. In alternative embodiments, the support arms 92 can be configured to pivot independently of each other about the horizontal pivot axis.

Figure 10:
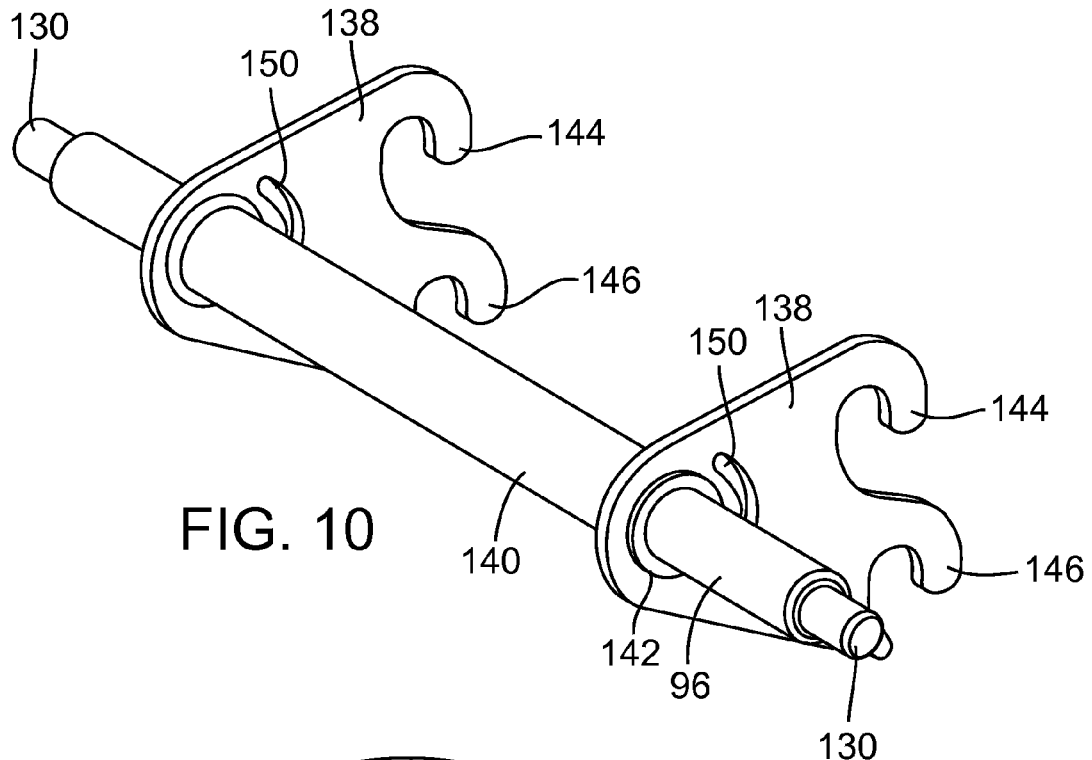
FIG. 10 is a perspective view of the bracket assembly for the arm support assembly.

As best shown in FIGS. 7 and 10, a bracket assembly 136 can be mounted on the shaft 96 between the pivot mechanisms 94. The bracket assembly 136 in the illustrated configuration is configured to allow the arm support assembly 42 to be removed from and placed on any of the rungs 32 (FIG. 3) to adjust the vertical position of the assembly 42.

Figure 12:
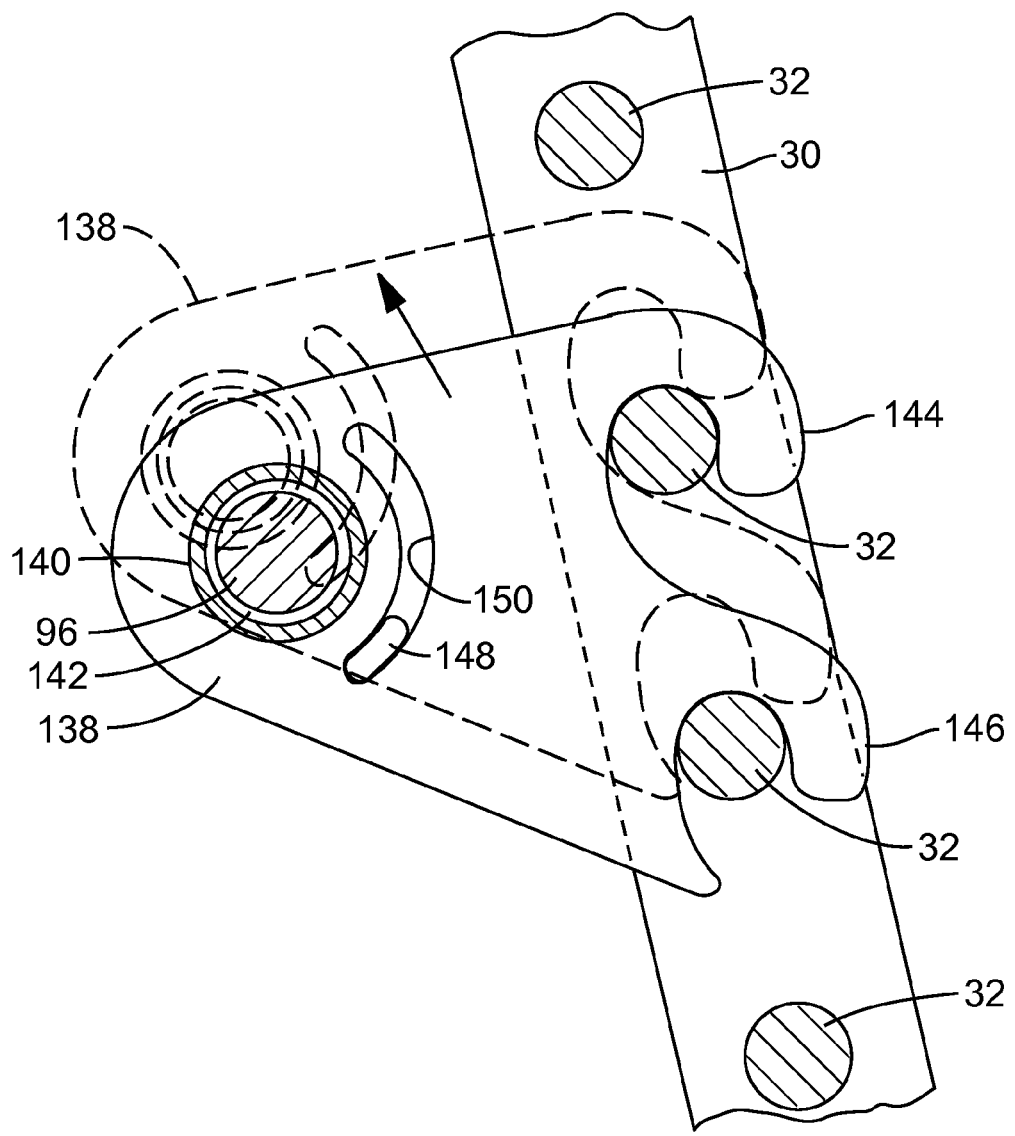
FIG. 12 is an enlarged side view showing one of the brackets of the bracket assembly mounted on horizontal rungs of the operating support.

The bracket assembly 136 in certain embodiments includes first and second spaced-apart brackets 138 secured to the ends of an elongated tubular cross member 140 that houses a central portion of the shaft 96. A bearing 142 can be disposed on the shaft 96 adjacent each bracket 138. As best shown in FIG. 12, each bracket 138 can be formed with curved hook portions 144 and 146 configured to be placed around horizontal rungs 32 for supporting the arm support assembly 42 on the frame structure 16. To remove or adjust the height of the arm support assembly 42, the assembly 42 is lifted up until the hook portions clear the rungs, and then moved rearwardly away from the rungs. The arm support assembly 42 can be supported on any two rungs to suit the needs of the user.

Upward and downward pivoting movement of the support arms 92 can be limited by a stop member 148 extending from each housing portion 132 into a curved opening or slot 150 formed in the adjacent bracket 138 (FIGS. 8 and 9). In use, the support arms 92 and the bearing housings 110 can be pivoted upwardly and downwardly about the horizontal pivot axis, with such motion being limited by the arc length of the slot 150. In alternative embodiments, only one stop member 148 and corresponding slot 150 can be provided since the support arms 92 in the illustrated embodiment are interconnected by shaft 96 to pivot together about the horizontal pivot axis.

In alternative embodiments, the arm supports 88a, 88b can be mounted for pivotal movement about respective vertical axes V but are prevented from pivoting upwardly and downwardly about a horizontal axis. In still other embodiments, the arm supports 88a, 88b can pivot about a horizontal axis but are prevented from pivoting about respective vertical axes.

The frame structure desirably has light-weight construction so that the operating support can be easily positioned for use and transported between operating theaters. As shown in the illustrated embodiment, the frame structure 16 can be constructed from tubular frame members desirably made from a light-weight material such as steel, aluminum or any of various suitable alloys. This provides a light-weight construction allowing for easy positioning and transporting of the operating support. In alternative embodiments, the frame structure can have a different construction that does not utilize tubular frame members.

FIGS. 13 and 14 illustrate the use of the operating support 10 for performing laparoscopic surgery, and in particular laparoscopic pelvic surgery, on a patient positioned on an operating table 12. As shown, the operating support 10 is positioned such that the front end portion of the operating table 12 extends beneath the seat 14. This allows the surgeon to sit at a position straddling the upper body of the patient. In this position, the surgeon can more easily manipulate the relatively long instruments used in laparoscopic surgery with less stress and strain on the surgeon's body. The position of the surgeon relative to the patient also provides other doctors or nurses access to the patient during the procedure, for example if the anesthesiologist must attend to the patient. If it becomes necessary during surgery to provide additional access to the upper body of the patient, for example if the anesthesiologist requires additional access to the patient, the surgeon can quickly move one of the arm supports 88a, 88b to its rearward and/or raised position to permit the surgeon to dismount the operating support. The operating support then can be easily moved away from the patient to provide other doctors or nurses additional access the patient.

In use, portions of the operating support 10 and/or the surgeon can be covered with a disposable, sterile drape to reduce the risk of contamination. For example, as shown in FIG. 2, separate drapes 160 can be provided to cover the arm supports 88a, 88b or portions thereof and a drape 162 can be provided to cover the chest support 54 or portions thereof. As shown in FIG. 13, another drape 164 can be provided to cover the patient and the legs of the surgeon. The drape 164 in the illustrated example has an opening and two side portions that extend around the waist of the surgeon and are tied off or otherwise connected to each other at the back of the surgeon, as indicated at 166. The size and shape of the drape 164 can be altered to suit the particular procedure being performed. Although not shown in FIG. 13, in a specific implementation, the drapes 160, 162 are used together with the drape 164. Following the medical procedure, the used drapes can be disposed of and replaced with new drapes.

The drapes can be made from any of various materials that are used for making commercially available surgical drapes, such as fabrics, polymeric materials, paper, or combinations thereof.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An operating support for a surgeon performing a medical procedure in combination with a patient operating table, the support comprising:
    a seat adapted to support the buttocks of the surgeon;
    first and second, laterally spaced foot supports adapted to support the feet of the surgeon while sitting in the seat, wherein each of the foot supports has a horizontally disposed foot pad for supporting a foot of the surgeon; and
    a frame structure supporting the seat and the foot supports;
    wherein the operating table comprises two opposing sides and an end portion extending perpendicularly from one side to the other side, the end portion being positioned beneath the seat and between the foot supports such that the foot supports are on opposite sides of the table and such that a surgeon, while sitting in the seat, can straddle a patient lying on the table.

2. The combination of claim 1, wherein the foot supports are configured to be vertically adjustable relative to the frame structure to permit adjustment of the height of the foot supports relative to the seat.

3. The combination of claim 1, wherein frame structure comprises first and second laterally spaced frame members supporting the first and second foot supports, respectively.

4. The combination of claim 3, further comprising respective wheels secured to the frame members for supporting the operating support on a floor.

5. The combination of claim 1, further comprising a chest support pad supported by the frame structure such that the angle of the chest support pad relative to a vertical plane can be adjusted to allow the surgeon to lean closer to or farther away from the patient.

6. The combination of claim 1, wherein the first and second foot supports are coupled to first and second laterally spaced frame portions, respectively, of the frame structure, the frame portions being spaced from each other such that the end portion of the operating table can be positioned between the frame portions.

7. The combination of claim 1, wherein the frame structure does not support the seat with any vertically extending support members positioned directly underneath the seat.

8. The combination of claim 1, wherein the seat is configured to be vertically adjustable relative to the frame structure to permit adjustment of the height of the seat relative to the operating table.

9. The combination of claim 1, wherein the frame structure comprises a chest support frame portion supporting a chest support, the chest support frame portion being supported for translational movement in a substantially, horizontal for-aft direction relative to the foot supports.

10. The combination of claim 1, further comprising one or more disposable sterile coverings placed over selected portions of the frame structure.

11. An operating support for a surgeon performing a medical procedure on a patient positioned on an operating table, the support comprising:
    a seat adapted to support the buttocks of the surgeon;
    first and second, laterally spaced foot supports adapted to support the feet of the surgeon while sitting in the seat; and
    a frame structure supporting the seat and the foot supports, the frame structure being configured to be positioned relative to the operating table such that an end portion of the operating table can be positioned between the foot supports and beneath the seat and the surgeon, while sitting in the seat, can straddle the patient;
    wherein the frame structure comprises a horizontally disposed seat frame supporting the seat and a chest support frame portion secured at a lower end thereof to a forward end of the seat frame, the chest support frame portion extending upwardly from the seat frame and supporting a chest support pad.

12. An operating support for a surgeon performing a medical procedure on a patient positioned on an operating table, the support comprising:
    a seat adapted to support the buttocks of the surgeon;
    first and second, laterally spaced foot supports adapted to support the feet of the surgeon while sitting in the seat;
    a frame structure supporting the seat and the foot supports, the frame structure being configured to be positioned relative to the operating table such that an end portion of the operating table can be positioned between the foot supports and beneath the seat and the surgeon, while sitting in the seat, can straddle the patient;
    first and second arm supports coupled to the frame structure and adapted to support the left and right arms of the surgeon; and
    a chest support coupled to the frame structure and adapted to support the chest of the surgeon while sitting in the seat, the chest support having an upper portion that extends above the arm supports.

13. The operating support of claim 12, further comprising one or more removable sterile surgical drapes covering one or both of the arm supports and the chest support.

14. The operating support of claim 12, wherein each of the arm supports is pivotably coupled to the frame structure and configured to pivot about a respective pivot axis between a respective first position adjacent the surgeon and a respective second position away from the surgeon.

15. The operating support of claim 12, wherein the arm supports are vertically adjustable to permit adjustment of the vertical position of the arm supports relative to the chest support.

16. An operating support for a surgeon performing a medical procedure in combination with a patient operating table, the support comprising:
    a frame structure; and
    a seat supported by the frame structure;
    first and second, laterally spaced foot supports supported by the frame structure and being adjustable in height relative to the seat;
    wherein the operating table comprises two opposing sides and an end portion extending perpendicularly from one side to the other side, the end portion being positioned beneath the seat and between the foot supports such that the foot supports are on opposite sides of the table and such that a surgeon, while sitting in the seat, can straddle a patient lying on the table.

17. An operating support for a surgeon performing a medical procedure on a patient positioned on an operating table, the support comprising:
    a frame structure; and
    a seat supported by the frame structure;
    first and second, laterally spaced foot supports supported by the frame structure and being adjustable in height relative to the seat;
    wherein the lateral spacing between the foot supports is such that an end portion of the operating table can be positioned between the foot supports and beneath the seat to allow the surgeon to straddle the patient at a position above and over the patient;
    further comprising a chest support frame portion supported at a lower end thereof at a location adjacent a front edge of the seat, the chest support frame portion extending upwardly from the seat and supporting a chest support configured to support the chest of the surgeon.

18. The operating support of claim 17, wherein the lower end of the chest support portion is attached to the frame structure at a location between the opposing sides of the seat.

19. The operating support of claim 17, further comprising first and second arm supports adapted to support the arms of the surgeon and coupled to the frame structure, the arm supports being vertically adjustable to permit adjustment of the vertical position of the arm supports relative to the chest support.

20. The operating support of claim 17, wherein the lower end of the chest support portion is connected to a horizontally disposed seat frame at a location along a line that extends from a front edge of the seat to a rear edge of the seat through the center of the seat.

21. A surgical system comprising:
    an operating table for supporting a patient, the operating table comprising two opposing sides and an end portion extending perpendicularly from one side to the other side; and
    a support apparatus for a surgeon performing a medical procedure on the patient, the support apparatus comprising a seat adapted to support the buttocks of the surgeon, left and right, laterally spaced foot supports adapted to support the feet of the surgeon, and means for supporting the seat at a position over and above an end portion of the operating table;

wherein the end portion of the table is positioned beneath the seat and between the foot supports such that the foot supports are on opposite sides of the table and such that a surgeon, while sitting in the seat, can straddle a patient lying on the table.

22. The system of claim 21, wherein the foot supports are configured to be vertically adjustable to permit adjustment of the height of the foot supports relative to the seat.

23. The system of claim 21, wherein the support apparatus comprises left and right arm supports adapted to support the arms of the surgeon, and a chest support configured to support the chest of the surgeon, the chest support having an upper portion that extends above the arm supports.

24. The system of claim 23, further comprising one or more disposable sterile coverings covering selected portions of the support apparatus.

25. An operating support for a surgeon performing a medical procedure on a patient positioned on an operating table, the support comprising:

a seat adapted to support the buttocks of the surgeon;

a frame structure supporting the seat and comprising first and second laterally spaced, vertically extending support members positioned on opposite sides of the seat such that an end portion of the operating table can be positioned between the support members and beneath the seat to allow the surgeon to straddle the patient at a position above and over the patient;

a chest support coupled to the seat and adapted to support the chest of the surgeon;

first and second foot supports adapted to support the feet of the surgeon, each of the first and second foot supports being mountable at a plurality of positions along the length of the first and second support members, respectively, so as to adjust the height of the foot supports relative to the seat; and the first and second arm supports adapted to support the arms of the surgeon, the first and second arm supports being pivotably connected to opposite end portions of a cross member, each arm support being pivotable about a respective vertically extending pivot axis to permit pivoting of the arm support between a respective forward position adjacent the surgeon for use and a respective second position away from the surgeon, the arm supports also being pivotable about a common horizontal pivot axis between a lowered position and a raised position, the cross member being supported by the frame structure and being vertically adjustable relative to the frame structure to permit adjustment of the height of the arm supports.

* * * * *